United States Patent [19]

Bruchmann et al.

[11] Patent Number: 5,484,916

[45] Date of Patent: Jan. 16, 1996

[54] PROCESS FOR THE PREPARATION OF ISOCYANATES CONTAINING URETDIONE GROUPS BY USING IMIDAZOLE GROUP CONTAINING POLYMERIC CATALYSTS

[75] Inventors: Bernd Bruchmann, Ludwigshafen; Roland Minges, Gruenstadt; Christian Schade, Ludwigshafen, all of Germany

[73] Assignee: BASF Aktiengesellschaft, Germany

[21] Appl. No.: 59,050

[22] Filed: May 10, 1993

[30] Foreign Application Priority Data

Jun. 5, 1992 [DE] Germany ............ 42 18 540.8

[51] Int. Cl.$^6$ .................................... C07D 229/00
[52] U.S. Cl. .............. 540/202; 525/186; 525/327.6
[58] Field of Search .............. 540/202; 525/186, 525/327.6

[56] References Cited

U.S. PATENT DOCUMENTS

| | | | |
|---|---|---|---|
| 3,290,288 | 12/1966 | Oertel et al. | 540/202 |
| 3,919,195 | 11/1975 | Bakhitov et al. | 540/202 |
| 4,336,365 | 6/1982 | Reischl et al. | 528/44 |
| 4,595,534 | 6/1986 | Scholl | 540/202 |
| 4,786,655 | 11/1988 | Grögler et al. | 528/45 |
| 4,797,455 | 1/1989 | Lin et al. | 525/504 |
| 4,894,429 | 1/1990 | Grögler et al. | 521/93 |
| 4,912,210 | 3/1990 | Disteldorf et al. | 540/202 |
| 4,929,724 | 5/1990 | Engbert et al. | 521/93 |
| 5,106,875 | 4/1992 | Horn et al. | 521/137 |
| 5,149,766 | 9/1992 | Bruchmann | 528/49 |

FOREIGN PATENT DOCUMENTS

| | | |
|---|---|---|
| 0317744A3 | 10/1988 | European Pat. Off. . |
| 0368217A3 | 11/1989 | European Pat. Off. . |
| 0417603A3 | 9/1990 | European Pat. Off. . |
| 0418639A1 | 9/1990 | European Pat. Off. . |
| 0431331A1 | 11/1990 | European Pat. Off. . |
| 46/37503 | 2/1968 | Japan . |
| 0100148 | 8/1976 | Poland . |
| 821158 | 9/1959 | United Kingdom . |

OTHER PUBLICATIONS

Synthesis, 463–464, 1975.
Recent Advances In Isocyanate Chemistry, Chemical Review, 47–73, 1957.
Chemical Abstracts Registry, 1994.
Dictionary of Organic Compounds, vol. 3, Fifth Edition, pp. 3287–3288, 1982.
Chemsources U.S.A., 1994 Edition.

*Primary Examiner*—Yogendra N. Gupta
*Attorney, Agent, or Firm*—Dennis V. Carmen

[57] ABSTRACT

In a process for the preparation of polyisocyanates containing uretdione groups by catalytic dimerization of monomeric isocyanates, the catalysts employed are polymers carrying imidazole groups.

6 Claims, No Drawings

PROCESS FOR THE PREPARATION OF ISOCYANATES CONTAINING URETDIONE GROUPS BY USING IMIDAZOLE GROUP CONTAINING POLYMERIC CATALYSTS

The present invention relates to a process for the preparation of polyisocyanates containing uretdione groups by catalytic dimerization of monomeric isocyanates.

The principle is known that uretdiones can be prepared by converting isocyanates in the presence of catalysts. Suitable catalysts are various substances, e.g. trialkylphosphines, as described in DE-A 30 05 106, trialkyl phosphites, as described in DE-A 23 49 726, triaminophosphines, as described in U.S. Pat. No. 3,290,288 and DE-A 34 37 635, cycloamidines, as described in JP-A 46/37 503, pyridine or substituted pyridines, as described in GB-A 821,158, and organometallic compounds, e.g. bismuth or antimony compounds, as described in DE-A 36 40 855 and DE-A 34 20 114.

The imidazoles and benzimidazoles as described in EP-A-0 417 603 have proven particularly suitable. They give high yields and high selectivity, in particular with respect to suppression of the formation of isocyanurates.

It is common to these known catalysts that the catalyst must be removed from the reaction mixture or deactivated by suitable measures after the dimerization. If the catalyst remains in the product, it may, by catalyzing undesired side reactions, interfere with the reactions in which the dimer is employed as starting material. In addition, the catalyst may evaporate or sublime out on thermal treatment of the isocyanates or the products prepared therefrom, which must be avoided due to the health risk posed by many of the catalysts.

The catalyst is usually removed during washing or recrystallization of the dimer. Since the product cannot be heated, removal of the catalyst by distillation is not possible. Washing of the uretdione requires considerable amounts of solvent. The catalyst must either be recovered from the large amounts of solvent or deactivated by suitable chemicals.

In the methods mentioned, recovery of the catalyst without significant losses is difficult. After deactivation, considerable amounts of the deactivated compound frequently remain in the product.

It is an object of the present invention to provide a process for the preparation of polyisocyanates containing uretdione groups which gives high yields and selectivities and in which the catalyst can easily be removed from the reaction mixture once the formation of the uretdione groups is complete, and can be re-used without complex work-up.

We have found that, surprisingly, this object is achieved by a process for the preparation of polyisocyanates containing uretdione groups in which the catalysts employed are polymers carrying terminal and/or lateral imidazole groups.

The present invention accordingly provides a process for the preparation of polyisocyanates containing uretdione groups by converting monomeric isocyanates in the presence of catalysts, wherein the catalysts employed are polymers which contain imidazole groups bonded terminally and/or laterally to the polymer chain.

In the polymeric compounds to be employed according to the invention as catalysts, the imidazole groups may be bonded to the polymer chain directly or via spacer groups; the imidazole groups may be unsubstituted or substituted.

Suitable polymer-bonded imidazole groups are, in particular, those which conform to the formula (I) or (II)

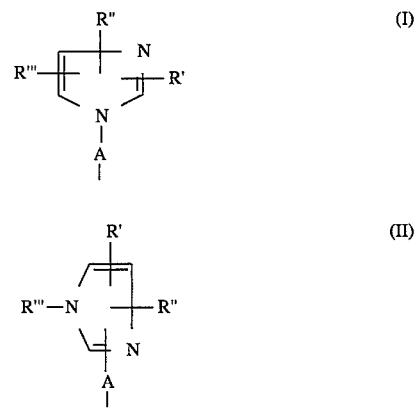

where

R', R", R''', are identical or different and, independently of one another, are hydrogen, $C_1$- to $C_{12}$-alkyl, aryl, $C_1$- to $C_{12}$-heteroalkyl, heteroaryl, $C_2$- to $C_{12}$-alkenyl, $C_2$- to $C_{12}$-alkynyl, an ether group, an ester group or halogen, or two of these radicals may be connected to one another in the form of a ring, for example with formation of a fused benzene ring, and A is a single chemical bond, $C_1$- to $C_{12}$-alkylene, arylene, $C_1$- to $C_{12}$-heteroalkylene, heteroarylene, $C_2$- to $C_{12}$-alkenylene, $C_2$- to $C_{12}$-alkynylene, sulfur, sulfinyl or sulfonyl.

The polymers to be employed according to the invention as catalysts can be prepared by polymerizing monomeric imidazoies carrying alkenyl groups, in particular vinyl or allyl groups, alone, in mixtures with one another or in mixtures with other copolymerizable vinyl or allyl monomers.

Suitable vinyl or allyl group-carrying monomeric imidazoles are those of the formula (III) or (IV)

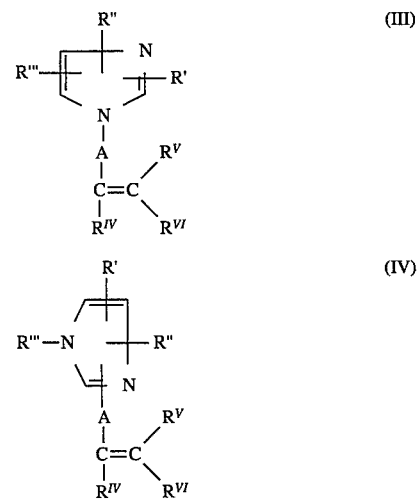

where

A, R', R", R''' are as defined above and $R^{IV}$, $R^V$ and $R^{VI}$ are identical or different and, independently of one another, are hydrogen, $C_1$- to $C_8$-alkyl, preferably $C_1$- to $C_4$-alkyl, aryl, preferably phenyl, halogen, in particular fluorene or chlorine, or groups containing a hetero atom, in particular oxygen and/or nitrogen, preferably ether, ester, keto or acid derivative groups, in particular nitrile groups.

Examples of monomeric imidazoles are 1-vinylimidazole, 4-vinylimidazole, 2-methyl-1-vinylimidazole, 4-methyl-1-vinylimidazole, 5-methyl-1-vinylimidazole, 2-ethyl-1-vinylimidazole, 2-propyl-1-vinylimidazole, 2-isopropyl-1-vinylimidazole, 2-phenyl-1-vinylimidazole, 1-vinyl-4,5-benzimidazole, 1-allylimidazole and 1-allyl-2-methylimidazole. Preference is given to 1-vinylimidazole, 2-methyl-1-vinylimidazole, 1-allylimidazole and 1-allyl-2-methylimidazole.

The monomeric imidazoles carrying alkenyl groups may also be polymerized in a mixture with further monomers carrying vinyl or allyl groups. Examples of such comonomers are aromatic monomers, such as styrene, alkyl (meth)acrylates, in particular having 1–20 carbon atoms in the alkyl group, e.g. stearyl acrylate, (meth)acrylates containing dialkylamino groups in the ester side chain, e.g. diethylaminoethyl acrylate, alkyl vinyl ethers having 1–18 carbon atoms in the alkyl group, N-vinylamides, such as N-vinylpyrrolidone and N-vinylcaprolactam, and N-alkyl and N,N-dialkylacrylamides. Particular preference is given to aromatic comonomers, e.g. styrene.

The polymers to be employed according to the invention as catalysts are advantageously prepared using a crosslinking component. Suitable comonomers for this purpose are polyethylenically unsaturated monomers, e.g. divinylbenzene, divinylethyleneurea, allyl (meth)acrylate or (meth)acrylates of organic compounds containing at least two OH groups in the molecule, for example (meth)acrylates of pentaerythritol, trimethylolpropane or bisphenol A.

For use according to the invention as catalysts, the proportion of imidazole-carrying monomer units in the polymer should generally be at least 0.5% by weight, preferably from 10 to 90% by weight, based on the polymer.

The polymers can be prepared by numerous processes, the principles of which are known from the literature. The monomers are expediently polymerized with one another at elevated temperature in a manner known per se using initiators which form free radicals. Particularly suitable methods are suspension polymerization, reverse suspension polymerization and precipitation polymerization.

Suspension polymers are obtained, for example, by suspending and reacting the monomers in an aqueous alkali metal salt solution. The properties of the resultant polymers can be modified as desired by adding organic precipitants or swelling agents, pore formers, e.g. ethyl acetate or n-butanol, and suitable protective colloids or emulsifiers to the polymerization batch.

In reverse suspension polymerization, the monomers are dissolved in water, and this phase is suspended and polymerized in an inert organic solvent, for example cyclohexane. It is favorable to add protective colloids or emulsifiers to the system. When the reaction is complete, the water can be removed, for example by azeotropic distillation, and the polymer isolated by filtration.

Another suitable preparation method is based on the use of a solvent which is capable of dissolving the monomers, but not the polymer. Suitable solvent systems of this type are ketones having 3–6 carbon atoms, alkyl esters having 3–12 carbon atoms, alcohols having 4–10 carbon atoms, dimethylformamide, dimethylacetamide, N-methylpyrrolidone, t-butyl methyl ether, $C_1$-$C_4$-monoalkyl and dialkyl ethers of mono- and oligoethylene glycols, aromatics solvents, such as benzene, xylene and toluene, halogenated hydrocarbons, such as 1,1,1-trichloroethane or methylene chloride, or $C_5$-$C_8$-hydrocarbons, or mixtures of these.

The polymerization is preferably carried out in the presence of a compound which forms free radicals. Examples for suitable initiators are hydrogen peroxide, inorganic persulfates and organic compounds of the peroxide or azo type. The molecular weight of the polymers can, if desired, be reduced by adding regulators to the reaction mixture.

The polymers prepared by these methods can generally be readily isolated, for example by filtration, and purified and dried by further suitable steps. In order to obtain an increased active surface area when the polymers are used according to the invention as catalysts, it is frequently appropriate to comminute the polymers, for example by grinding to a particle size of from 10 to 250 μm, preferably from 20 to 150 μm, before they are used in the process according to the invention.

In order to positively modify certain properties of the imidazole group-containing polymers, for example the heat and solvent resistance or abrasion behavior, they can be used in mixtures with commercially available polymers, e.g. polyethylene, polypropylene, polyvinyl chloride, polytetrafluoroethylene or polyether ketone. These blends are prepared in a manner known per se.

A further method of preparing the imidazole group-containing polymers according to the invention is to react imidazoles containing reactive groups with polymers whose chains contain terminal and/or lateral groups which are capable of reacting with the reactive groups of the imidazoles.

The polymers carrying terminal and/or lateral imidazole groups are employed according to the invention as catalysts in the conversion of monomeric isocyanates for the preparation of polyisocyanates containing uretdione groups.

The monomeric isocyanates are dimerized in the presence or absence of an aprotic solvent. The catalyst concentration should be at least 0.001% by weight, usually from 0.01 to 5% by weight, based on the monomeric isocyanate.

The isocyanates which can be employed are aromatic isocyanates, e.g. phenyl isocyanate, tolyl isocyanate, 1,5-naphthalene diisocyanate, 1,4-phenylene diisocyanate, 2,4-tolylene diisocyanate (2,4-TDI), 2,6-tolylene diisocyanate (2,6-TDI), 4,4'-diphenylmethane diisocyanate (4,4'-MDI), and 2,4'-diphenylmethane diisocyanate (2,4'-MDI), individually or as mixtures with one another.

The solvents employed are aprotic organic solvents, in particular benzene, toluene, acetone, methyl ethyl ketone, chloroform, alkyl acetates, n-, iso- or cycloalkanes, or chlorobenzene.

The dimerization usually commences quickly after the catalyst has been added to the isocyanate, which, if desired, is in solution. When the dimerization is complete, the polymeric catalyst can according to the invention be removed very simply from the reaction mixture, for example by rapidly filtering the catalyst off when the reaction mixture begins to become cloudy. The polyisocyanate containing uretdione groups can then be crystallized out by cooling the reaction solution. The crystals are removed, for example, by filtration. The separated-off product is washed with an aprotic organic solvent and then dried, under reduced pressure in order to avoid thermal decomposition. The recovered catalyst can be re-used, without further treatment, for the next reaction batch.

It is also possible to carry out the dimerization continuously by passing the isocyanate, if desired in solution, over the polymeric catalyst in the form of a fixed bed.

If the catalytic activity of the catalyst drops due to contamination with isocyanates or reaction products, it can be freed from adherent products by treatment with a solvent or by heating and thus reactivated.

The process according to the invention can be carried out simply and without problems. Surprisingly, the polymer catalysts to be employed according to the invention have very high activities and selectivities, give pure end products without the need for particular purification, and are reusable.

The invention is illustrated in greater detail by the examples below, in which parts are by weight, unless stated otherwise.

EXAMPLE 1

Preparation of the polymeric catalysts

The following polymer catalysts were prepared (see also Table 1).

A) Copolymer of 1-vinylimidazole (1) and styrene, 50:50, crosslinked by means of divinylethyleneurea (DVEH)

B) Copolymer of 1-vinylimidazole (1) and bisphenol A diacrylate (BADA), 80:20

C) Copolymer of 2-methyl-1-vinylimidazole (2) and styrene, 66:33, crosslinked by means of DVEH D) Copolymer of 2-methyl-1-vinylimidazole (2) and styrene, 20:80, crosslinked by means of DVEH E) Copolymer of 1-allyl-2-methylimidazole (3) and BADA, 83:17.

TABLE 1

Batches for the preparation of the catalysts

| Polymer | Batch |
|---|---|
| A | 200 g of ethyl acetate<br>75 g of imidazole 1<br>75 g of styrene<br>7.5 g of DVEH<br>1.5 g of AIBN (azobisisobutyronitrile) |
| B | 250 g of ethyl acetate<br>150 g of imidazole 1<br>30 g of BADA<br>4 g of AIBN |
| C | 200 g of n-butanol<br>100 g of imidazole 2<br>50 g of styrene<br>7.5 g of DVEH<br>1.5 g of AIBN |
| D | 200 g of n-butanol<br>30 g of imidazole 2<br>120 g of styrene<br>7.5 g of DVEH<br>1.5 g of AIBN |
| E | 250 g of ethyl acetate<br>150 g of imidazole 3<br>30 g of BADA<br>4 g of AIBN |

Procedure for the preparation of the catalysts

The solution of 1,100 g of water and 200 g of sodium sulfate was introduced into a heatable reactor fitted with a stirrer, and nitrogen was bubbled through the solution. The respective batch (see Table 1) was added with stirring, and the mixture was heated to 70° C. The mixture was stirred at 70° C. for 22 hours.

After the reaction mixture had been cooled, the resultant polymer was isolated by means of a suction filter, washed several times with water and then dried for 16 hours at 60° C. under reduced pressure. It was subsequently ground to a particle size of <250 μm.

EXAMPLE 2

Dimerization of the isocyanates
General reaction conditions:

1,000 g of diisocyanate, 5 g of polymer catalyst and, if desired, 1,000 g of solvent, in each case as stated in Table 2, were warmed to 40° C. and stirred for 2 hours. The catalyst was then filtered off with suction. On cooling to 20° C., the dimer crystallized out as a solid. After 12 hours, it was filtered off with suction, washed with toluene or methyl ethyl ketone (MEK) and dried at 60° C. under reduced pressure.

The uretdiones still contained traces of adhering monomers. Isocyanurates, which cause mostly undesired crosslinking when the uretdiones are used in polyurethane systems, 20 were below the detection limit (about 1%).

TABLE 2

Dimerization reaction data and dimer product data

| Isocyanate | Solvent | Catalyst | Yield [%] | Melting point [°C.] |
|---|---|---|---|---|
| 2,4-TDI | Toluene | A | 15 | 155–158 |
| 2,4-TDI | — | B | 12 | 155–158 |
| 2,4-TDI | MEK | C | 30 | 157–159 |
| 2,4-TDI and 2,6-TDI in the ratio 80:20 | Toluene | D | 10 | 156–158 |
| 2,4-TDI | — | E | 35 | 156 |
| 2,4-TDI | MEK | E | 45 | 156–158 |
| 2,4-TDI | Toluene | E | 40 | 156 |
| 4,4'-MDI | MEK | E | 42 | 256–275 |

EXAMPLE 3

Reusability of the catalyst systems 1,000 g of 2,4-TDI, 10 g of catalyst E and 1,000 g of methyl ethyl ketone were stirred for 1 hour at 40° C. The catalyst was filtered off with suction (filtrate 1) and reemployed at 40° C. in a mixture of 1,000 g of 2,4-TDI and 1,000 g of methyl ethyl ketone. After 1 hour, the catalyst was again filtered off with suction (filtrate 2), boiled with toluene and then with methyl ethyl ketone and reemployed with 1,000 g of 2,4-TDI and 1,000 g of methyl ethyl ketone. The catalyst was filtered off with suction to give the filtrate 3. Cooling of the filtrates to 20° C. caused the TDI dimer to crystallize out. After 12 hours, this was filtered off with suction and treated further as described in Example 2. The melting points of the dimers were from 156° to 158° C.

The following yields were achieved:

Filtrate 1: 520 g (52%)

Filtrate 2: 280 g (28%)

Filtrate 3: 390 g (39%).

We claim:

1. A process for the preparation of polyisocyanates containing uretdione groups by dimerizing aromatic monomeric isocyanates in the presence of catalysts, wherein the catalysts employed comprise polymeric compounds to whose polymer chains imidazole groups are bonded terminally and/or laterally and which have been prepared by polymerizing alkenyl group-containing imidazoles, alone or together with vinyl monomers.

2. A process as claimed in claim 1, wherein the imidazole groups are unsubstituted or substituted.

3. A process as claimed in claim 2, wherein the imidazole group-containing polymers employed as catalyst are employed as a mixture with conventional polymers.

4. A process as claimed in claim 1, wherein the imidazole group-containing polymers employed as catalysts are mixed with conventional polymers.

5. A process as claimed in claim 2, wherein the imidazole group-containing polymers employed as catalysts are mixed with conventional polymers.

6. The process of claim 1, wherein said imidazole groups are substituted with hydrogen, $C_1$ to $C_{12}$-alkyl, aryl, aralkyl, alkaryl, $C_1$ to $C_{12}$-heteroalkyl, heteroaryl, $C_1$ to $C_{12}$-alkenyl, and/or $C_1$ to $C_{12}$-alkynyl.

* * * * *